United States Patent
Sabina et al.

(10) Patent No.: US 10,987,202 B2
(45) Date of Patent: Apr. 27, 2021

(54) UNITARY DENTAL MODEL

(71) Applicant: Align Technology, Inc., San Jose, CA (US)

(72) Inventors: Michael Sabina, Campbell, CA (US); Avi Kopelman, Palo Alto, CA (US); Yoram Sharabi, Kadima (IL)

(73) Assignee: ALIGN TECHNOLOGY, INC., San Jose, CA (US)

(*) Notice: Subject to any disclaimer, the term of this patent is extended or adjusted under 35 U.S.C. 154(b) by 317 days.

(21) Appl. No.: 16/006,183

(22) Filed: Jun. 12, 2018

(65) Prior Publication Data

US 2018/0289455 A1    Oct. 11, 2018

Related U.S. Application Data

(62) Division of application No. 14/306,096, filed on Jun. 16, 2014, now Pat. No. 10,016,262.

(51) Int. Cl.
*A61C 13/34* (2006.01)
*A61C 13/00* (2006.01)
(Continued)

(52) U.S. Cl.
CPC .......... *A61C 13/34* (2013.01); *A61C 13/0004* (2013.01); *A61C 8/0001* (2013.01); *A61C 9/0053* (2013.01); *G16H 20/40* (2018.01)

(58) Field of Classification Search
CPC ....... A61C 13/34; A61C 13/12; A61C 13/081; A61C 13/0027; A61C 13/0004; A61C 8/001; A61C 9/0053
(Continued)

(56) References Cited

U.S. PATENT DOCUMENTS 2,467,432 A   4/1949   Kesling
3,407,500 A   10/1968  Kesling
(Continued)

FOREIGN PATENT DOCUMENTS

AU    3031677 A     5/1979
AU     517102 B2    7/1981
(Continued)

OTHER PUBLICATIONS

AADR. American Association for Dental Research, Summary of Activities, Mar. 20-23, 1980, Los Angeles, CA, p. 195.
(Continued)

*Primary Examiner* — Nicholas D Lucchesi
(74) *Attorney, Agent, or Firm* — Wilson Sonsini Goodrich & Rosati

(57) ABSTRACT

Improved dental models for use in dental procedures are provided. In one aspect, a unitary dental model of an intraoral cavity of a patient having a dental implant comprises a physical surface representative of gingival tissue of the patient. The model can comprise a channel shaped and oriented to receive an abutment corresponding to a physical abutment to be connected to the dental implant, in which the channel extends to an opening in the physical surface. The channel can comprise a first portion shaped to receive and constrain a corresponding structure of the abutment to a position and orientation and a second portion shaped to receive a fastener to couple the abutment to the unitary dental model. In many embodiments, the first portion comprises a shoulder shaped to receive the corresponding structure of the abutment in order to position the abutment along the channel.

23 Claims, 10 Drawing Sheets

(51) Int. Cl.
*G16H 20/40* (2018.01)
*A61C 8/00* (2006.01)
*A61C 9/00* (2006.01)

(58) Field of Classification Search
USPC .................................................. 433/213, 214
See application file for complete search history.

(56) References Cited

U.S. PATENT DOCUMENTS

| | | |
|---|---|---|
| 3,458,936 A | 8/1969 | Schulz et al. |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,934,347 A | 1/1976 | Lash et al. |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,398,884 A | 8/1983 | Huffman |
| 4,459,110 A | 7/1984 | Jackson |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,521,188 A | 6/1985 | Metzler |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,721,464 A | 1/1988 | Roden et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 4,997,370 A | 3/1991 | Mayclin |
| 5,011,405 A | 4/1991 | Lemchen |
| 5,017,133 A | 5/1991 | Miura |
| 5,027,281 A | 6/1991 | Rekow et al. |
| 5,030,102 A | 7/1991 | Lang |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,286,191 A | 2/1994 | Poveromo |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,513,989 A | 5/1996 | Crisio |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,457 A | 2/1997 | Bailey et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,123 A | 3/1998 | Blacklock et al. |
| 5,733,126 A | 3/1998 | Andersson et al. |
| 5,740,267 A | 4/1998 | Echerer et al. |
| 5,742,700 A | 4/1998 | Yoon et al. |
| 5,775,899 A | 7/1998 | Huffman |
| 5,788,490 A | 8/1998 | Huffman |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |

(56) References Cited

U.S. PATENT DOCUMENTS

| | | |
|---|---|---|
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,283,753 B1 | 9/2001 | Willoughby |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,428,318 B2 | 8/2002 | Artal et al. |
| 6,482,298 B1 | 11/2002 | Bhatnagar |
| 6,524,101 B1 | 2/2003 | Phan et al. |
| 6,554,611 B2 | 4/2003 | Shishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 6,788,986 B1 | 9/2004 | Traber et al. |
| 8,403,667 B2 | 3/2013 | Adams |
| 8,419,430 B2 | 4/2013 | Pogorelsky |
| 8,465,283 B2 | 6/2013 | Adams |
| 8,509,932 B2 | 8/2013 | Kopelman |
| 8,612,037 B2 | 12/2013 | Powell et al. |
| 9,763,758 B2 | 9/2017 | Kopelman et al. |
| 10,016,262 B2 | 7/2018 | Sabina et al. |
| 2002/0006597 A1 | 1/2002 | Andreiko et al. |
| 2003/0009252 A1 | 1/2003 | Pavlovskaia et al. |
| 2003/0036035 A1 | 2/2003 | Chen |
| 2003/0139834 A1 | 7/2003 | Nikolskiy et al. |
| 2003/0224311 A1 | 12/2003 | Cronauer |
| 2004/0128010 A1 | 7/2004 | Pavlovskaia et al. |
| 2005/0055118 A1 | 3/2005 | Nikolskiy et al. |
| 2006/0093988 A1* | 5/2006 | Swaelens ............... A61C 1/084 433/76 |
| 2007/0015105 A1 | 1/2007 | Campanello |
| 2008/0038692 A1* | 2/2008 | Andersson .......... A61C 13/0013 433/167 |
| 2008/0108014 A1 | 5/2008 | Holzner et al. |
| 2009/0092948 A1* | 4/2009 | Gantes ................... A61C 1/084 433/215 |
| 2011/0294093 A1 | 12/2011 | Herweg et al. |
| 2012/0135373 A1 | 5/2012 | Cheng et al. |
| 2013/0164704 A1 | 6/2013 | Kim |
| 2013/0216980 A1 | 8/2013 | Boronkay et al. |
| 2013/0289950 A1 | 10/2013 | Kopelman |
| 2014/0032183 A1 | 1/2014 | Fisker et al. |
| 2014/0038135 A1 | 2/2014 | Kopelman |
| 2014/0124969 A1 | 5/2014 | Blaisdell et al. |
| 2014/0205969 A1 | 7/2014 | Marlin |
| 2015/0359615 A1 | 12/2015 | Sabina et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | 08508174 | 9/1996 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-0008415 A1 | 2/2000 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Operation & Training Manual. Great Lakes Orthodontics, Ltd. 199 Fire Tower Drive, Tonawanda, New York. 14150-5890, 20 pages total (1990).

(56) References Cited

OTHER PUBLICATIONS

Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for gingiva. Dictionary.com p. 1-3. Retrieved from the internet Nov. 5, 2004<http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC—Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet<http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.

(56) References Cited

OTHER PUBLICATIONS

Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy as One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
NASH, "CEREC CAD/CAM Inlays: Aesthetics and Durability in a Single Appointment," Dent. Today, 9(8):20, 22-23, (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.

Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).

(56) References Cited

OTHER PUBLICATIONS

The Choice is Clear: Red, White & Blue . . . The Simple, Affordable, No-Braces Treatment, Allesee HJ Orthodontic Appliances—Pro Lab product information for patients,<http://ormco.com/aoa/appliancesservices/RWB/patients.html>, 2 pages (May 19, 2003).

The Choice Is Clear: Red, White & Blue . . . The Simple, Affordable, No-Braces Treatment, Allesee Orthodontic Appliances—Pro Lab product information, 6 pages (2003).

The Red, White & Blue Way to Improve Your Smile! Allesee Orthodontic Appliances—Pro Lab product information for patients, 2 pages 1992.

Truax L., "Truax Clasp-Less(TM) Appliance System," Funct. Orthod., 9(5):22-4, 26-8 (Sep.-Oct. 1992).

Tru-Tain Orthodontic & Dental Supplies, Product Brochure, Rochester, Minnesota 55902, 16 pages total (1996).

U.S. Department of Commerce, National Technical Information Service, "Automated Crown Replication Using Solid Photography SM," Solid Photography Inc., Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden, "A New Method to Determine Tooth Positions and Dental Arch Dimensions," J. Dent. Res., 51(4):1104 (Jul.-Aug. 1972).

Van Der Linden et al., "Three-Dimensional Analysis of Dental Casts by Means of the Optocom," J. Dent. Res., p. 1100 (Jul.-Aug. 1972).

Van Der Zel, "Ceramic-Fused-to-Metal Restorations with a New CAD/CAM System," Quintessence Int., 24(11):769-778 (1993.

Varady et al., "Reverse Engineering of Geometric Models—An Introduction," Computer-Aided Design, 29(4):255-268,1997.

Verstreken et al., "An Image-Guided Planning System for Endosseous Oral Implants," IEEE Trans. Med. Imaging, 17(5):842-852 (Oct. 1998).

Warunek et al., Physical and Mechanical Properties of Elastomers in Orthodonic Positioners, Am J. Orthod. Dentofac. Orthop, vol. 95, No. 5, (May 1989) pp. 399-400.

Warunek et.al., Clinical Use of Silicone Elastomer Applicances, JCO (1989) XXIII(10):694-700.

Wells, Application of the Positioner Appliance in Orthodontic Treatment, Am. J. Orthodont. (1970) 58:351-366.

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).

Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).

You May Be a Candidate for This Invisible No-Braces Treatment, Allesee Orthodontic Appliances—Pro Lab product information for patients, 2 pages (2002).

* cited by examiner

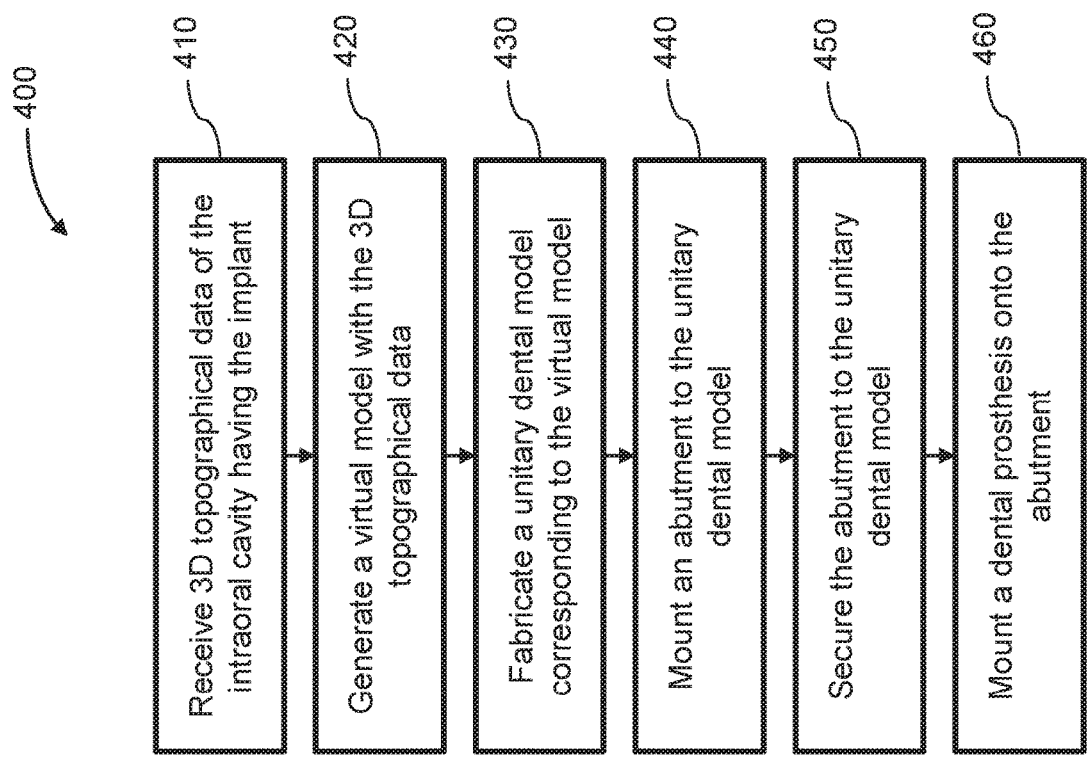

UNITARY DENTAL MODEL

CROSS-REFERENCE

This application is a divisional application of U.S. application Ser. No. 14/306,096, filed Jun. 16, 2014, now U.S. Pat. No. 10,016,262, issued Jul. 10, 2018, which is incorporated herein by reference in its entirety, and to which application we claim priority under 35 USC § 121.

BACKGROUND

Dental implants are widely used as artificial substitutes for the root portion of missing teeth. A dental implant allows a dental restoration, such as a dental prosthesis, to be securely anchored to the jaw via an abutment mounted to the implant. An endosseous implant may have an externally threaded body. The threaded body can be configured for self-tapping into the bone tissues of the jaw. An endosseous implant can have an internal passage that is configured, such as internally threaded, for receiving and securing the anchoring stem of a permanent abutment therein.

Following implantation of an implant in the intraoral cavity and healing of the surrounding tissues, a physical model of the intraoral cavity is produced for facilitating design and manufacture of the permanent abutment and prosthesis that are to be mounted onto the implant. In one procedure, an analog is placed in the physical model that is similar to the patient's intraoral cavity. The analog can be configured with an internal passage similar to the internal passage of the implant for receiving and securing the permanent abutment. The dental technician can then use the physical model to design and/or build a dental prosthesis for the patient. The dental technician mounts an abutment to the physical model via the internal passage of the analog. The dental technician then proceeds to build a dental prosthesis to fit onto the abutment and match surrounding teeth in the intraoral cavity of the patient.

The methods and apparatus for constructing dental models can be less than ideal in at least some instances. Accurate placement of the analog in the physical model can be important for correct design and manufacture of the permanent abutment and prosthesis, and also for the outcome of the dental procedure. Accurate placement of an analog into a physical dental model, however, can be difficult. For example, manual positioning and orientation of an analog can be less than ideal with respect to accuracy, outcome and user convenience. In some dental models, which may employ a separate implant analog that is separately coupled to the dental model, inaccuracies in the placement of such implant analogs may compromise the accurate positioning of the abutment, and therefore degrade the accuracy of the prosthesis subsequently fabricated on the abutment and model.

Thus, there is a need for improved dental models for dental procedures involving a dental implant. Ideally, such improved models would be simple to use, provide improved outcomes, include relatively few discrete parts, and provide accurate positioning and orienting of the permanent abutment.

SUMMARY

Embodiments of the present invention provide improved dental models and methods for dental procedures. The embodiments disclosed herein simplify the coupling of an abutment for a dental implant to a physical dental model, thereby enhancing the accuracy and ease of placement of the abutment in the model. In many embodiments, a unitary dental model of a patient's intraoral cavity comprises integrally formed structures shaped to position and orient the abutment relative to the model, and the position and orientation may comprise a predetermined position and orientation. The unitary model may comprise integrally formed structures shaped to receive a fastener in order to secure the abutment to the dental model. These structures can facilitate direct coupling of the abutment to the dental model in a configuration corresponding to the configuration of the abutment and implant in the patient's intraoral cavity, so as to provide an accurate model of abutment placement in the intraoral cavity suitable for use in dental prosthesis design and fabrication. Direct fabrication of a physical model having the structures described herein can decrease the number of steps performed to couple a separate implant analog to a physical model of a patient's dentition, which can reduce the probability of error associated with manual analog placement and providing for simpler and more accurate design and/or fabrication of dental prostheses mounted to dental implants.

Thus, in one aspect, a unitary dental model of an intraoral cavity of a patient having a dental implant is provided. The model comprises a physical surface representative of gingival tissue of the patient. The model can comprise a channel shaped and oriented to receive an abutment corresponding to a physical abutment to be connected to the dental implant, in which the channel extends to an opening in the physical surface. The channel comprises a first portion shaped to receive and constrain a corresponding structure of the abutment to a position and orientation and a second portion shaped to receive a fastener to couple the abutment to the unitary dental model. In many embodiments, the first portion comprises a shoulder shaped to receive the corresponding structure of the abutment in order to position the abutment along the channel.

Other objects and features of the present invention will become apparent by a review of specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 illustrates a method for creating a unitary dental model of a patient's intraoral cavity, in accordance with many embodiments;

DETAILED DESCRIPTION

Figure 1A:
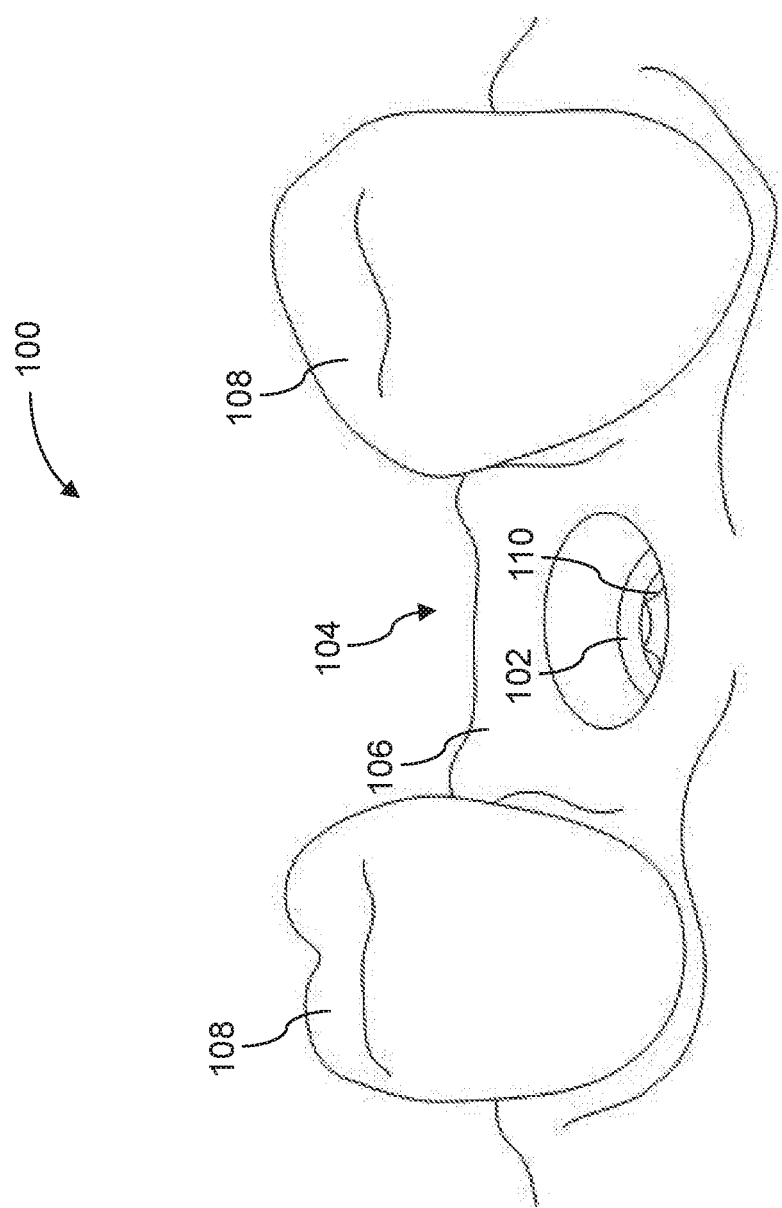
FIG. 1A illustrates a portion of a patient's intraoral cavity having an implant, in accordance with many embodiments.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different example and aspects of the present disclosure. It should be appreciated that the scope of the disclosure includes other embodiments not discussed in detail above. Various other modifications, changes, and variations which will be apparent to those skilled in the art may be made in the arrangement, operation, and details of the embodiments of the present disclosure provided herein without departing from the spirit and scope of the invention as described herein.

As used herein A and/or B encompasses one or more of A, or B, and combinations thereof such as A and B.

The embodiments disclosed herein can be combined in one or more of many ways to provide improved dental models for use in various dental procedures. A unitary dental model of a patient's intraoral cavity having one or more dental implants can comprise a channel having a first portion shaped to receive and constrain an abutment to a position and orientation and a second portion shaped to receive a fastener for coupling the abutment to the model. The structures of the channel in the dental model can facilitate placement of the abutment with greater accuracy and using fewer parts. The methods and systems described herein can decrease additional components and/or interfaces to mount a separate implant analog to a physical model of the patient's dentition.

While the present description is directed to a single implant, the embodiments described herein can be used to create virtual and physical dental models of an intraoral cavity with any number of dental implants. For example, some embodiments described herein can be used with a plurality of implants that are functionally independent from one another (e.g., being used for separate prostheses). Alternatively or in combination, some embodiments can be used with a plurality of implants where at least some of the implants are functionally dependent (e.g., being used together for a bridge prosthesis or other prostheses spanning multiple teeth). Exemplary dental prostheses suitable for use with the embodiments disclose herein include crowns, bridges, dentures, or any other abutment-supported prosthetic devices, for example.

In many embodiments, a unitary dental model of an intraoral cavity of a patient having a dental implant is provided. The model can include a physical surface representative of gingival tissue of the patient. The model can also include a channel shaped and oriented to receive an abutment corresponding to a physical abutment to be connected to the dental implant, the channel extending along to an opening in the physical surface. The channel may comprise a first portion shaped to receive and constrain a corresponding structure of the abutment to a position and orientation within the first portion, and a second portion shaped to receive a fastener to couple the abutment to the unitary dental model. In many embodiments, the first portion comprises a shoulder shaped to receive the corresponding structure of the abutment in order to position the abutment along the channel.

The design of the unitary dental model may be varied as desired. For instance, in many embodiments, the physical surface comprises physical models of one or more teeth and a physical model of gingival tissue extending between the one or more teeth. The physical models of the one or more teeth may be representative of one or more teeth of the intraoral cavity near the implant, such as one or more teeth adjacent the implant site. The opening can comprise a maximum cross-sectional dimension sized larger than a maximum cross-sectional dimension of the second portion. The first portion can be shaped to correspond to a portion of the dental implant that receives and constrains a corresponding portion of the physical abutment. The second portion can extend to an opening in a bottom surface opposite the physical surface. The opening in the bottom surface can be shaped to accommodate a nut for securing the abutment and fastener to the unitary dental model.

As described above, the unitary dental model can be configured to engage an abutment so as to constrain it to a desired position and orientation. In many embodiments, the first portion is shaped to receive and constrain the corresponding structure of the abutment to a predetermined position and orientation. The predetermined position and orientation may correspond to a position and orientation of the physical abutment when connected to the dental implant in the intraoral cavity. The channel may be an elongate channel comprising a longitudinal axis, and the predetermined position and orientation can be defined by one or more of the longitudinal axis, shoulder, or opening. The predetermined orientation may comprise a rotation about the longitudinal axis or a rotation away from the longitudinal axis. In many embodiments, the corresponding structure of the abutment comprises a lower engagement surface and the shoulder is shaped to receive and mate with the lower engagement surface in order to position the corresponding structure at a location along the longitudinal axis. Optionally, the model can include the abutment comprising the corresponding structure comprising the lower engagement surface In many embodiments, a computer-implemented method for creating a virtual model of an intraoral cavity of a patient having a dental implant is provided. The method comprises receiving three-dimensional (3D) topographical data of the intraoral cavity having the dental implant. A virtual model can be generated with the 3D topographical data. The virtual model can comprises a virtual surface representative of gingival tissue of the patient and a channel shaped and oriented to receive a virtual abutment model corresponding to one or more of a physical abutment to be connected to the dental implant or an abutment to be connected to a unitary dental model fabricated from the virtual model. The channel can extend to an opening in the surface and can comprise a first portion and a second portion. The first portion can be shaped to receive and constrain a corresponding structure of the virtual abutment model to a position and orientation. The second portion can be shaped to receive a virtual fastener model corresponding to a fastener used to couple the abutment to the unitary dental model. The first portion can comprise a shoulder shaped to receive the corresponding structure of the virtual abutment model in order to position the virtual abutment model along the channel.

Various techniques can be used to create the virtual models described herein. For instance, the step of using the 3D topographical data to create a virtual model may comprise positioning a virtual model of an implant analog relative to an as-scanned 3D virtual model that embodies the 3D topographical data of the intraoral cavity having the implant so that the implant analog virtual model matches the position and orientation of the implant in the as-scanned 3D virtual model. The as-scanned 3D virtual model can be modified by merging the implant analog virtual model with the as-scanned 3D virtual model, thereby creating a modified as-scanned model. Furthermore, using the 3D topographical data to create a virtual model may further comprise subtracting an extraction virtual model from the modified as-scanned model so as to at least one of: a) create the second portion of the channel shaped to receive the virtual fastener model, and b) remove one or more virtual model elements corresponding to a scan body or an impression body coupled with the implant in the as-scanned virtual model.

In many embodiments, a method for creating a unitary dental model of an intraoral cavity of a patient having a dental implant is provided. The method comprises receiving 3D topographical data of the intraoral cavity having the implant and fabricating the unitary dental model with the 3D topographical data. The unitary dental model can comprise a physical surface representative of gingival tissue of the patient. The model can also comprise a channel shaped and oriented to receive an abutment corresponding to a physical abutment to be connected to the dental implant, the channel extending to an opening in the physical surface. The channel can comprise a first portion shaped to receive and constrain a corresponding structure of the abutment to a position and orientation, and a second portion shaped to receive a fastener to couple the abutment to the unitary dental model. In many embodiments, the first portion comprises a shoulder shaped to receive the corresponding structure of the abutment in order to position the abutment along the channel. Optionally, the method may further comprise mounting the abutment to the unitary dental model via the first portion of the channel and securing the abutment to the unitary dental model using the fastener received within the second portion of the channel.

In many embodiments, the unitary dental model can be created based on a virtual model. For example, the step of using the 3D topographical data to fabricate the unitary dental model may comprise positioning a virtual model of an implant analog relative to an as-scanned 3D virtual model that embodies the 3D topographical data of the intraoral cavity having the implant so that the implant analog virtual model matches the position and orientation of the implant in the as-scanned 3D virtual model. The as-scanned 3D virtual model can be modified by merging the implant analog virtual model with the as-scanned 3D virtual model, thereby creating a modified as-scanned model. Furthermore, using the 3D topographical data to create a virtual model may further comprise subtracting an extraction virtual model from the modified as-scanned model so as to at least one of: a) create the second portion of the channel shaped to receive the virtual fastener model, and b) remove one or more virtual model elements corresponding to a scan body or an impression body coupled with the implant in the as-scanned virtual model. Optionally, using the 3D topographical data to create a virtual model may further comprise modifying one or more portions of the modified as-scanned model in order to provide a desired amount of clearance between the first portion and the corresponding structure of the abutment. The fabricating step may be performed using a computer-controlled material removing process.

In many embodiments, a system for modeling of an intraoral cavity of a patient having a dental implant is provided. The system includes one or more processors and memory storing instructions executable by the one or more processors. The instructions may cause the one or more processors to receive 3D topographical data of the intraoral cavity having the implant and generate a virtual model with the 3D topographical data. The virtual model can comprise a virtual surface representative of gingival tissue of the patient and a channel shaped and oriented to receive a virtual abutment model corresponding to one or more of a physical abutment to be connected to the dental implant or an abutment to be connected to a unitary dental model fabricated from the virtual model. The channel can extend to an opening in the surface and can comprise a first portion and a second portion. The first portion can be shaped to receive and constrain a corresponding structure of the virtual abutment model to a position and orientation. The second portion can be shaped to receive a virtual fastener model corresponding to a fastener used to couple the abutment to the unitary dental model. The first portion can comprise a shoulder shaped to receive the corresponding structure of the virtual abutment model in order to position the virtual abutment model along the channel.

In many embodiments, the instructions may cause the one or more processors to position a virtual model of an implant analog relative to an as-scanned 3D virtual model that embodies the 3D topographical data of the intraoral cavity having the implant so that the implant analog virtual model matches the position and orientation of the implant in the as-scanned 3D virtual model. The as-scanned 3D virtual model can be modified by merging the implant analog virtual model with the as-scanned 3D virtual model, thereby creating a modified as-scanned model. Furthermore, using the 3D topographical data to create a virtual model may further comprise subtracting an extraction virtual model from the modified as-scanned model so as to at least one of: a) create the second portion of the channel shaped to receive the virtual fastener model, and b) remove one or more virtual model elements corresponding to a scan body or an impression body coupled with the implant in the as-scanned virtual model.

In many embodiments, the instructions can cause the one or more processors to generate output configured to control a fabrication machine to fabricate a unitary dental model corresponding to the virtual model.

Turning now to the drawings, in which like numbers designate like elements in the various figures, FIG. 1A illustrates a portion of a patient's intraoral cavity 100 having an implant 102, in accordance with many embodiments. The implant 102 is positioned at an implant site 104 in the tissue of the intraoral cavity. The implant 102 can be a screw, post, cylinder, or any other device suitable for serving as an anchor for a dental prosthesis. The implant site 104 may correspond to the location of one or more missing teeth to be replaced by the dental prosthesis to be coupled to the implant 102. The implant site 104 can be located within the gingival tissue 106 extending between one or more teeth 108. Alternatively, the implant site 104 can be located within a wholly edentulous portion of the intraoral cavity, such that there are no teeth adjacent to or near the gingival tissue 106.

In many embodiments, the implant 102 includes a coupling interface 110 that is exposed from the surrounding gingival tissue 106. The coupling interface 110 can include structures suitable for coupling the implant 102 to a discrete component, such as a healing abutment, scan body, impression body, temporary abutment, or permanent abutment. The structures of the coupling interface 110 can be shaped to mate with corresponding structures of the discrete component, and can include any suitable combination of sockets, channels, apertures, grooves, notches, threads, and so on.

Figure 1B:
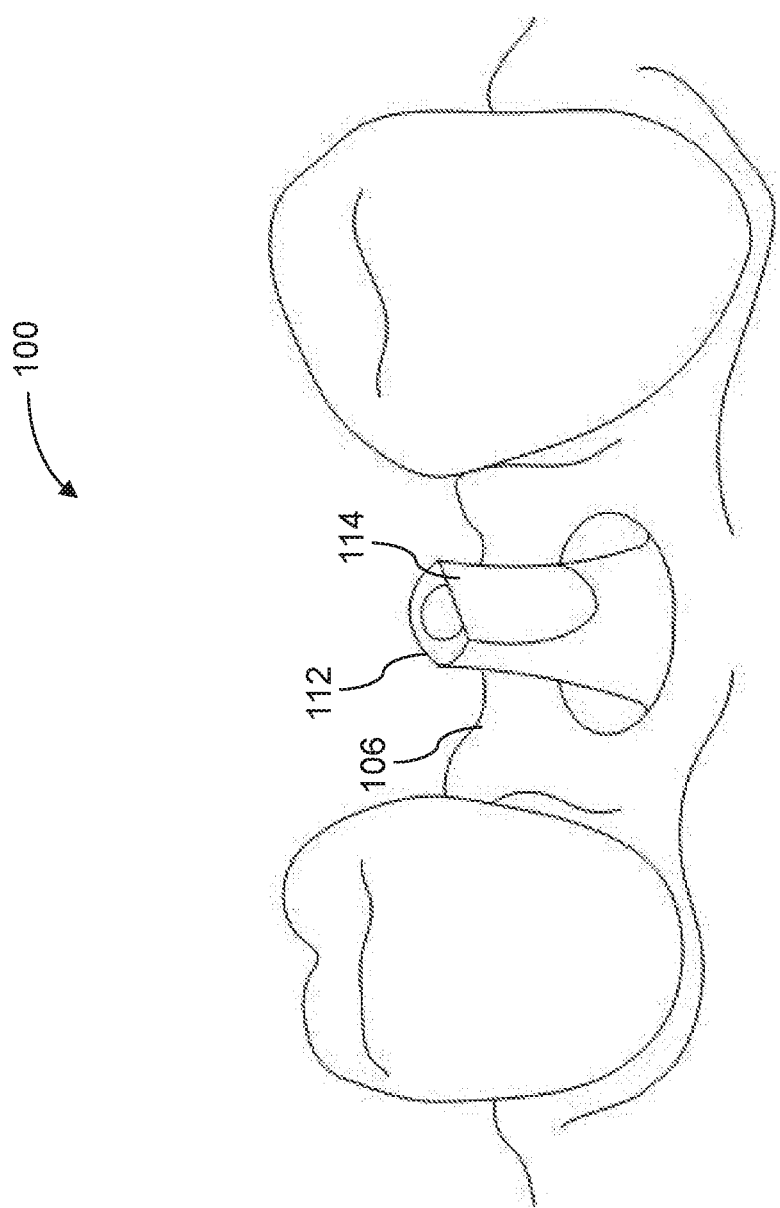
FIG. 1B illustrates a scan body or impression body coupled to an implant, in accordance with many embodiments.

FIG. 1B illustrates a scan body or impression body 112 coupled to the implant 102, in accordance with many embodiments. The scan body or impression body 112 can be coupled to the implant 102 via the coupling interface 110. The scan body or impression body 112 may protrude above the gingival tissues 106 such that its arrangement relative to the intraoral cavity can be captured using an intraoral scan or dental impression, respectively. The scan body or impression body 112 can include structures 114 enabling the position and orientation of the underlying implant 102 relative to the intraoral cavity to be determined based on the position and orientation of the structures 114. For instance, the structures 114 can include a shape or structure of the body 112 (e.g., an asymmetric shape), coloring, marks, symbols, characters, or any other visual markings or physical structures suitable for use with the body 112. The scan body or impression body 112 can be used in conjunction with intraoral scanning techniques or dental impression techniques, respectively, to produce topographical data of the intraoral cavity 100, as well as position and orientation information for the implant 102, as discussed in further detail below.

Figure 1C:
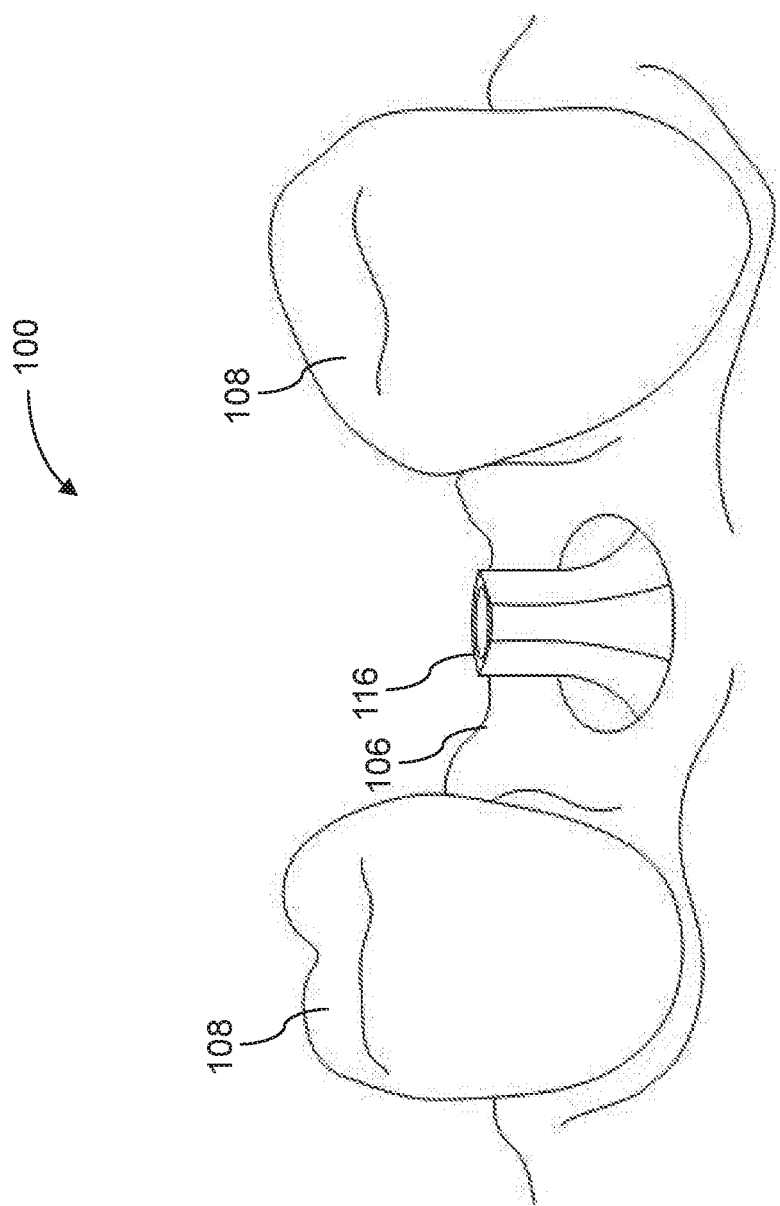
FIG. 1C illustrates an abutment coupled to an implant, in accordance with many embodiments.

FIG. 1C illustrates an abutment 116 coupled to the implant 102, in accordance with many embodiments. In many embodiments, the implant 102 serves as an anchor for a dental prosthesis such as a bridge or crown. The abutment 116 can serve as a support for the dental prosthesis as well as a connector for fastening the prosthesis to the implant. In many embodiments, the abutment 116 is coupled to the implant 102 (e.g., via the coupling interface 110), and the prosthesis (not shown) is mounted onto the abutment 116. The abutment 116 can be any suitable abutment for a dental procedure, such as a stock abutment manufactured with a predefined shape. Alternatively, the abutment 116 can be a custom abutment designed specifically for the patient. In many embodiments, the abutment 116 is manufactured through a computer-controlled process. The abutment 116 can be created based on the 3D data of the intraoral cavity and/or virtual modeling techniques, such as the techniques described herein, to ensure proper positioning and fit within the patient's intraoral cavity. The abutment 116 can be further modified to engage a portion of a dental prosthesis. For example, the upper surface of the abutment 116 can be refined as appropriate to interface with an interior surface of a crown to be seated onto the abutment 116.

In many embodiments, the abutment 116 is situated at a specified position and orientation relative to the intraoral cavity 100 (e.g., teeth 108, gingival tissues 106). The position and orientation of the abutment 116 may be determined based on the position and orientation of the implant 102 within the intraoral cavity 100. For example, the coupling interface 110 of the implant 102 can be shaped to receive a corresponding structure of the abutment 116 (e.g., a base portion of the abutment 116). The engagement between the coupling interface 110 and the corresponding structure of the abutment 116 can constrain the abutment 116 to the desired position and orientation.

As previously described, dental prostheses for an intraoral implant can be fabricated using a physical model of the patient's intraoral cavity. The use of such dental models allows such prostheses to be designed in conformance with the geometry of the intraoral tissues near the implant site (e.g., adjacent teeth and gingiva) so as to avoid collisions or interference, ensure proper bite registration, and provide the desired aesthetic appearance. During the prosthesis design process, the prosthesis can be mounted to the dental model via an abutment placed in the model. The abutment may correspond to or be the actual physical abutment that will be connected to the implant in the patient's intraoral cavity. The position and orientation of the abutment relative to the intraoral tissues represented in the model may correspond to the position and orientation of the actual abutment relative to the adjacent intraoral tissues when connected to the implant in the intraoral cavity.

In many embodiments, the dental models provided herein include integrally formed structures shaped and oriented to receive the abutment, such as a suitably shaped channel, cavity, passage, etc. The integrally formed structures can be designed to engage with and constrain the coupled abutment to a specified position and orientation. For example, the structures can include any suitable combination of shoulders, stops, recesses, notches, grooves, protrusions, or other such registration structures or features configured to engage and retain the abutment at the specified position and orientation. The position and orientation of the coupled abutment may be predetermined based on the position and orientation of the actual physical abutment when connected to the implant, as described above. Notably, the use of such integrally formed structures enables the abutment to be directly coupled to the model, thereby obviating the need for implant analogs that are placed into the model to interface with the abutment. Accordingly, embodiments of the models presented herein may be considered to be "unitary" models, in that the structures receiving and constraining the abutment to the desired position and orientation are integral with the model and not provided separately as discrete components.

In many embodiments, the integrally formed structures correspond to the corresponding structures of the implant coupling interface that engage the abutment. Any structure or combination of structures suitable for registering the abutment to a specified orientation and position can be used. For example, the structures can include a cavity defining a shape of at least a portion of the implant (e.g., the coupling interface of the implant). The structures can be symmetric or asymmetric, and can form a single continuous shape or multiple discontinuous shapes. The structures can include any suitable markers or indicators, for example, to aid a user in aligning and mounting the abutment onto the physical model.

Figure 2B:
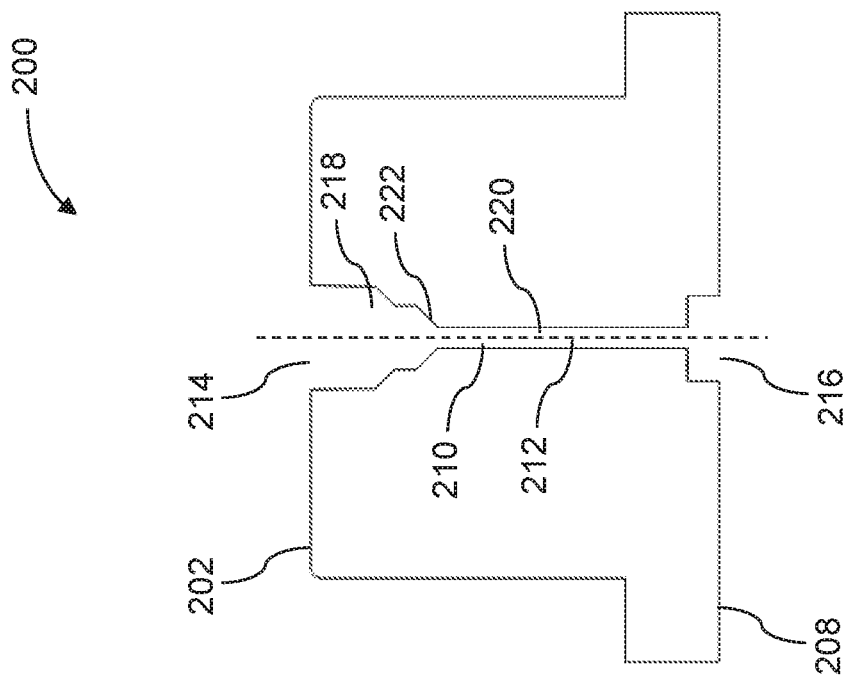
FIG. 2B is a cross-sectional view of the model of FIG. 2A, in accordance with many embodiments.
Figure 2A:
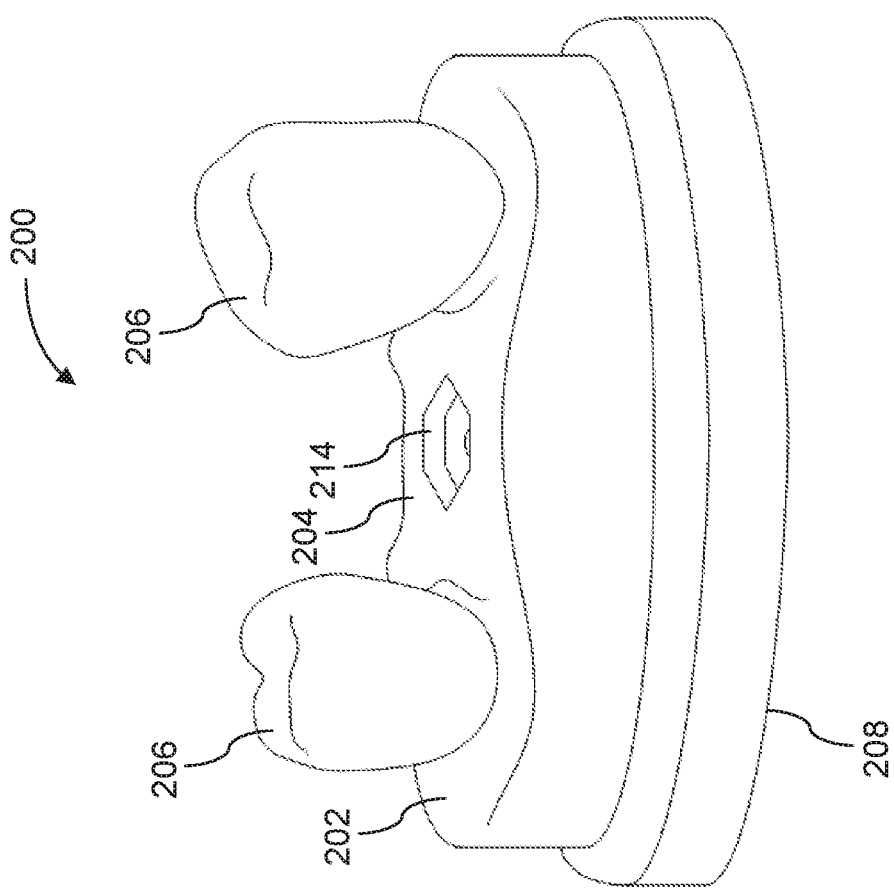
FIG. 2A illustrates a unitary dental model of an intraoral cavity with an implant, in accordance with many embodiments.

FIGS. 2A and 2B illustrate a unitary dental model 200 of an intraoral cavity with an implant, in accordance with many embodiments (FIG. 2B is a cross-sectional view of FIG. 2A). The unitary dental model 200 may be a positive physical model of the patient's intraoral cavity. The dental model 200 can depict any suitable portion of the patient's intraoral cavity, such as a portion of a dental arch (e.g., the upper or lower arch) or the entire dental arch. The dental model 200 can include a physical surface 202 representative of the patient's intraoral tissues near the implant site, such as gingival tissues 204. Optionally, the physical surface 202 can also include one or more tooth models 206 corresponding to teeth near the implant site. The physical surface 202 may be the upper surface of the dental model 200. The dental model 200 can also include a bottom surface 208 opposite the physical surface 202 forming part of a model base that supports the model 200 (e.g., when placed on a table, workbench, or other work surface).

In many embodiments, the model 200 includes a channel 210 formed at or near the implant site and shaped and oriented to receive an abutment. The channel 210 can be an elongate channel having a longitudinal axis 212. The channel 210 can extend at least partially through the thickness of the model 200 along the longitudinal axis 212. For example, a first end of the channel 210 can extend to an opening 214 in the physical surface 202. The opposing second end of the channel 210 can extend to an opening 216 in the bottom surface 208, such that the channel 210 extends through the entire thickness of the model 200. Alternatively, the second end of the channel 210 may not be connected to the bottom surface 208, such that the opening 216 is absent and the channel 210 extends only partially through the thickness of the model 200. The channel 210 can include a first portion 218 and a second portion 220. The first portion 218 can be connected to the opening 212 and can be configured to receive at least a portion of the abutment. For instance, the first portion 218 can include a shoulder 222 or other mechanical stop structure shaped to receive a corresponding structure of the abutment so as to position it along the channel 210. The second portion 220 can be connected to the first portion 218 via the shoulder 222 and can be shaped to receive a fastener for securing the abutment to the model 200. The maximum cross-sectional dimension (e.g., diameter) of the opening 214 and/or first portion 218 may be larger than the maximum cross-sectional dimension of the second portion 220. Optionally, the second portion 220 can be connected to the opening 216 in the bottom surface 208. The opening 216 can be shaped to receive a second fastener for securing the abutment.

Figure 2D:
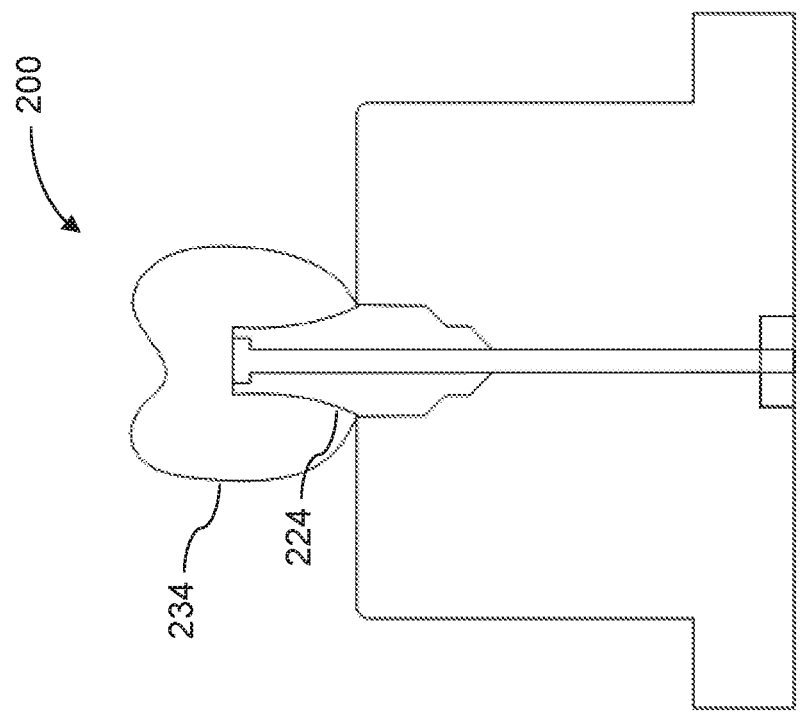
FIG. 2D illustrates a cross-sectional view of the model of FIG. 2A illustrating an abutment and dental prosthesis mounted thereto, in accordance with many embodiments.
Figure 2C:
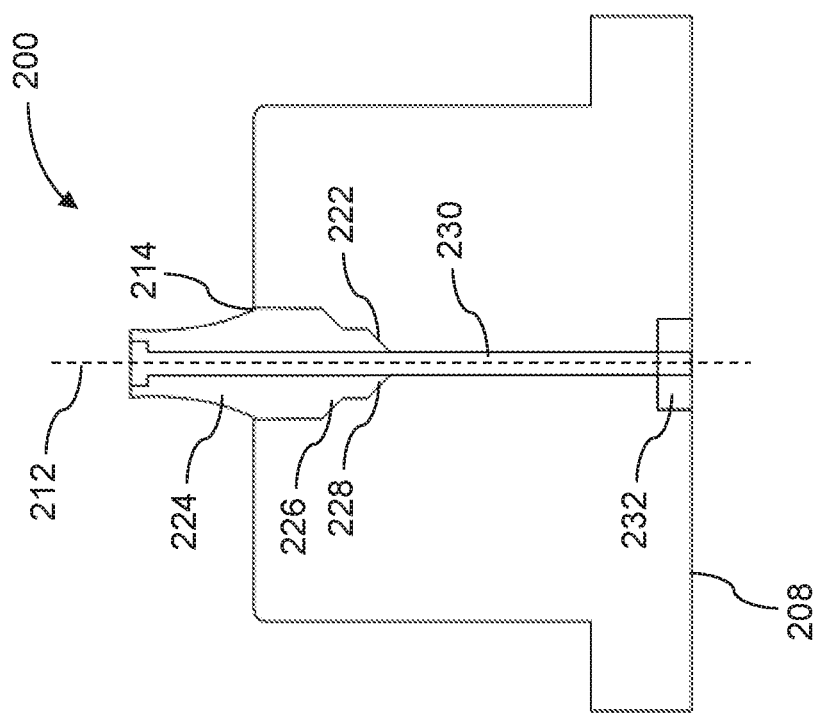
FIG. 2C is a cross-sectional view of the model of FIG. 2A illustrating an abutment mounted thereto, in accordance with many embodiments.

FIG. 2C illustrates an abutment 224 coupled to the unitary dental model 200, in accordance with many embodiments. Various components of the model 200 (e.g., channel 210, longitudinal axis 212, opening 214, and/or first portion 218) can be configured to constrain the abutment 224 to a position and orientation when mounted to the model 200 (e.g., a predetermined position and orientation as described above). The position and orientation of the abutment 224 can be defined with respect to up to six degrees of freedom of movement (e.g., three degrees of translation, three degrees of rotation). For example, the position of the abutment 224 may include a translation parallel to the longitudinal axis 212 and/or orthogonal to the longitudinal axis 212. As another example, the orientation of the abutment 224 may include a rotation about the longitudinal axis 212 or away from the longitudinal axis 212.

In many embodiments, the geometry and arrangement of the channel 210, longitudinal axis 212, opening 214, and/or first portion 218 define the position and orientation of the coupled abutment 224. For example, the shape of the opening 214 and/or the first portion 218 can be complementary to the shape of a corresponding structure of the abutment 224 (e.g., the lower or base portion 226 of the abutment 224) so as to define the position and orientation of the abutment when it is received into the opening 214 and/or first portion 218. The shape of the opening 214 and/or first portion 218 may correspond to the shape of a portion of the dental implant (e.g., the coupling interface) that receives and constrains the abutment structure. In many embodiments, the shoulder 222 can be shaped to receive and mate with a lower engagement surface 228 of a corresponding abutment structure so as to position the abutment along the channel 210 (e.g., along the longitudinal axis 212). The shoulder 222 may serve as a mechanical stop, such that the depth to which the abutment 224 is inserted along the channel 210 is constrained by the location of the shoulder 222. The geometry of the shoulder 222 may be complementary to the shape of the lower engagement surface 228 of the abutment. One or more portions of the engagement surface 228 may be inclined relative to the longitudinal axis 212, orthogonal or approximately orthogonal to the longitudinal axis 212, and so on.

The abutment 224 can be coupled to the unitary dental model 200 using a fastener 230. The second portion 220 of the channel 210 can be shaped to accommodate the fastener 230. For example, the second portion 220 can include a recess, channel, passage, cavity, etc., which may have a geometry (e.g., length, width, depth, diameter) corresponding to the geometry of the fastener 230. The fastener 230 can be a screw, bolt, pin, post, cylinder, etc. that passes through the abutment 224 (e.g., via a hole formed in the abutment 224) and the second portion 220 of the channel 210 so as to secure the abutment 224 to the model 200. For example, fastener 230 may be a self-tapping screw capable of being fastened to the material of the model 200 surrounding the second portion 220. As another example, the fastener 230 may be specifically configured to be used with the abutment 224, such as a screw that can be also used to couple the abutment 224 to the implant in the patient's intraoral cavity. In many embodiments, the opening 216 in the bottom surface 208 can be shaped to accommodate a second fastener, such as a nut 232. When placed in the model 200, the abutment 224, fastener 230, and nut 232 may be coaxial or approximately coaxial. The nut 232 can be tightened around the fastener 230 to secure the fastener 230 and abutment 224 to the model 200. This approach may advantageously permit a generic screw, threaded sleeve, or other fastener to be used to couple the abutment 224 without requiring self-tapping. Optionally, the channel 210 can include structures that permit the abutment 224 to be secured to the model 200 without the use of additional fasteners, such as integrated threading complementary to threading on a corresponding structure of the abutment.

FIG. 2D illustrates a dental prosthesis 234 mounted onto the model 200, in accordance with many embodiments. The dental prosthesis 234 can include an interior cavity shaped to receive a corresponding structure (e.g., the upper portion) of the abutment 224. As previously described, the dental prosthesis 234 can be fabricated using the model 200 and coupled abutment 224.

Various methods can be used for the design and fabrication of the unitary dental models described herein. For example, computer-based design methods can be used to develop virtual dental models that are subsequently used as input for computer-controlled manufacturing processes to produce the corresponding physical dental models. The use of such digital design and fabrication methods can provide convenient, flexible, and accurate production of dental models having the features presented herein.

Figure 3:
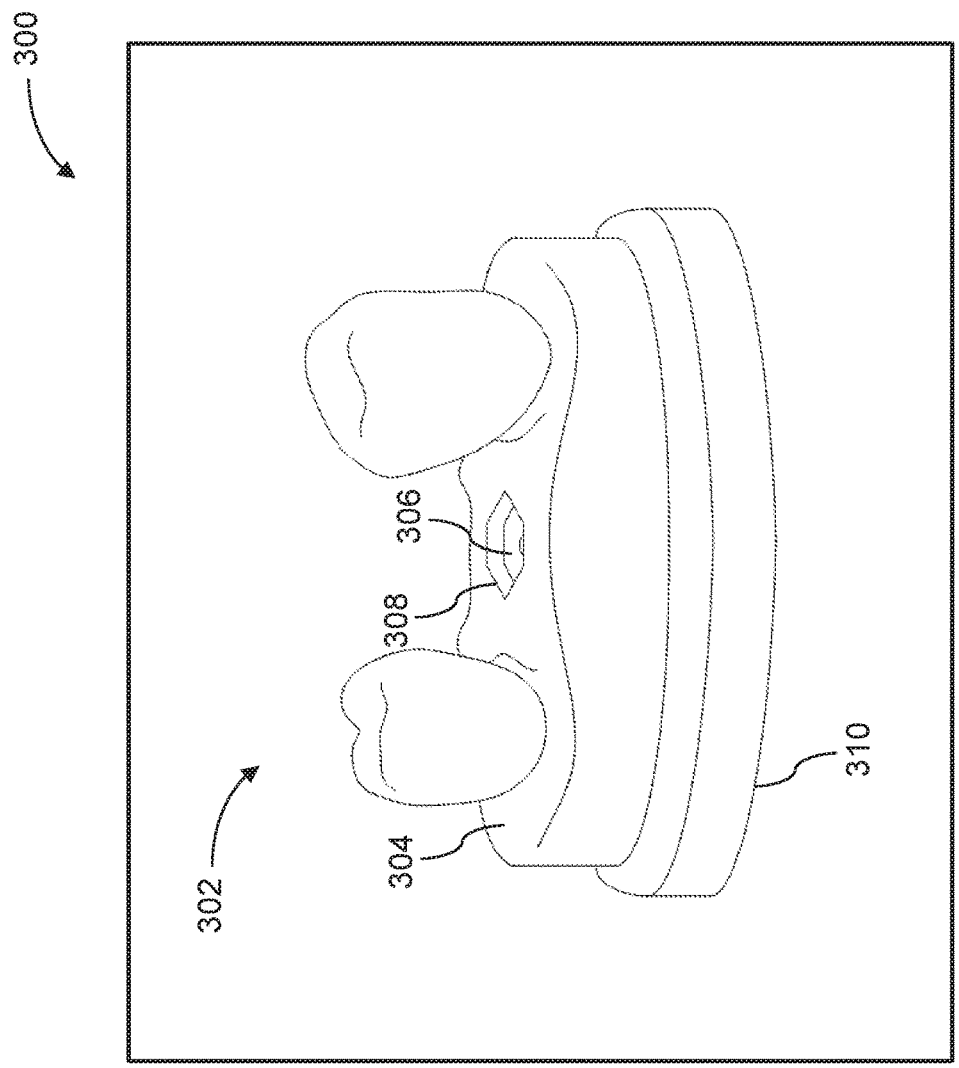
FIG. 3 illustrates a display showing a virtual model of a patient's intraoral cavity, in accordance with many embodiments.

FIG. 3 illustrates a display 300 showing a virtual model 302 of a patient's intraoral cavity, in accordance with many embodiments. The virtual model 302 can be used to design and fabricate a physical model, such as the unitary dental models provided herein. Accordingly, the virtual model 302 can include a virtual representation of any of the components of the physical models described herein. For example, the virtual model 302 can include a virtual surface 304 representative of intraoral tissues (e.g., virtual gingival tissues, virtual tooth models). The virtual model 302 can also include virtual structures shaped and oriented to receive a virtual abutment corresponding to the abutment to be connected to the implant and/or the abutment to be connected to the unitary dental model. For instance, the virtual model 302 can include a channel 306 extending to an opening 308 in the virtual surface 304, and optionally to an opening (not shown) in a virtual bottom surface 310 of the virtual model 302. The channel 306 can include any of the structures and features previously discussed herein, such as a first portion, second portion, shoulder, longitudinal axis, etc.

FIG. 4 illustrates a method 400 for creating a unitary dental model of a patient's intraoral cavity, in accordance with many embodiments. The method 400, as with all methods described herein, can be used in combination with any of the devices and systems described herein.

In step 410, three-dimensional (3D) topographical data of an intraoral cavity having an implant is received. The 3D topographical data can include any suitable surface of the intraoral cavity, such as a complete dentition, a partial dentition, and/or gingival tissues. In many embodiments, the 3D topographical data can include 3D topographical data of a suitable device coupled to the implant, such as an impression body or a scan body. As previously described, an impression body or scan body may include structures from which the orientation and position of the underlying implant can be determined relative to the patient's intraoral cavity.

The 3D topographical data can be obtained using any suitable method, such as an intraoral scan of the patient's dentition and implant. In many embodiments, the intraoral scan utilizes a handheld probe for measuring 3D surface topography by confocal focusing of light beams, for example, as disclosed in WO 2000/008415, the contents of which are incorporated herein in their entirety. Alternatively, a negative impression can be taken of the patient's teeth and scanned using any suitable method or device, such as by the probe described herein or a desktop scanner. In many embodiments, a positive model is made from the negative impression and scanned as described herein. For example, a stone model can be made from the negative impression and scanned (e.g., using a probe, desktop scanner, etc.) Alternatively, the 3D topographical data can be obtained in any other suitable manner, including other suitable intraoral scanning techniques, based on optical methods, direct contact methods or any other means. For example, X-ray-based, CT-based, MRI-based, or any other suitable type of scanning can be used to produce 3D topographical data of the patient's dentition and implant.

In step 420, a virtual model of the intraoral cavity is generated with the 3D topographical data. Any suitable method for producing a 3D virtual model from 3D topographical data (e.g., 3D scanning data) can be used, such as a method utilizing suitable computer-aided design (CAD) and/or computer-aided manufacturing (CAM) software. For example, the 3D topographical data can be used to determine a virtual surface of the 3D virtual model corresponding to intraoral tissues such as teeth or gingiva. The 3D virtual model can be modified to remove various model elements present in the 3D topographical data that will not be represented in the unitary dental model. For example, the 3D topographical data may include data corresponding to a scan body or impression body coupled to the implant that is removed prior to performing the following steps.

Furthermore, the 3D virtual model can be modified to incorporate various structures not represented by the 3D topographical data, such as the integrally formed structures for retaining an abutment and/or fasteners described herein. The integrally formed structures in the virtual model can be shaped and oriented to receive and constrain a virtual abutment model (corresponding to the abutment for the implant and/or unitary dental model) at a specified position and orientation. The design of the integrally formed structures may be determined based on information regarding the position and orientation of the implant in the intraoral cavity. Such information can be provided, for instance, using data of a scan body or impression body coupled to the implant, as previously described. Further details on the creation of a virtual model are provided below.

In step 430, a unitary dental model corresponding to the virtual model is fabricated. Any suitable fabrication method can be used, such as a computer-controlled manufacturing process. In many embodiments, a suitable additive manufacturing (AM) process (e.g., stereolithography, 3D printing, rapid prototyping) is used to directly fabricate the unitary dental model as a matching physical copy of the virtual model. Alternatively or in combination, a material removing process (e.g., a computer-controlled material removing process such as computerized numerical control (CNC) milling) can be used to fabricate the dental model. The fabrication method may be selected based on a desired fabrication resolution in order to ensure that the surfaces and structures of the dental model are produced with sufficient accuracy. For example, the fabrication resolution of a suitable fabrication method may be approximately 50 μm or less.

In many embodiments, a CNC milling process is used to fabricate the unitary dental model from a milling blank made of a suitable material, such as polyurethane. The CNC milling process may utilize a CNC milling machine which uses a drill bit (e.g., a 1 mm circular drill bit) to selectively remove material from the blank so as to form the surface contours of the unitary dental model. The instructions for controlling the CNC milling machine may be generated based on the 3D virtual model including the integrally formed structures for retaining an abutment and/or fasteners described herein (e.g., channel 210, openings 214, 216). Optionally, one or more portions of the 3D virtual model may be modified to ensure proper fit of the abutment with the integrally formed structures. For example, the 3D virtual model can be adjusted (e.g., by modifying the size and/or shape of one or more portions; by adding extensions, protrusions, recesses, etc.) to provide a specified minimum clearance between one or more portions of the abutment and the corresponding portions of the unitary dental model. Alternatively or in combination, the instructions for the milling machine may include a suitable amount of offset from one or more surfaces of the 3D virtual model so as to achieve the desired minimum clearance in the resultant dental model. In many embodiments, the minimum clearance between the unitary dental model and the abutment is less than or equal to approximately 500 μm. The minimum clearance can be selected to ensure that the abutment can be mounted to the model at the position and orientation defined by the integrally formed structures.

Figure 5A:
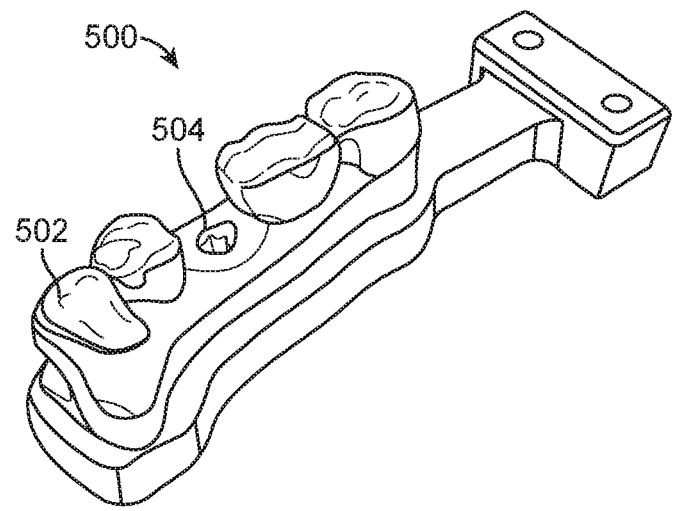
FIG. 5A illustrates a unitary dental model fabricated using a milling process, in accordance with many embodiments.
Figure 5B:
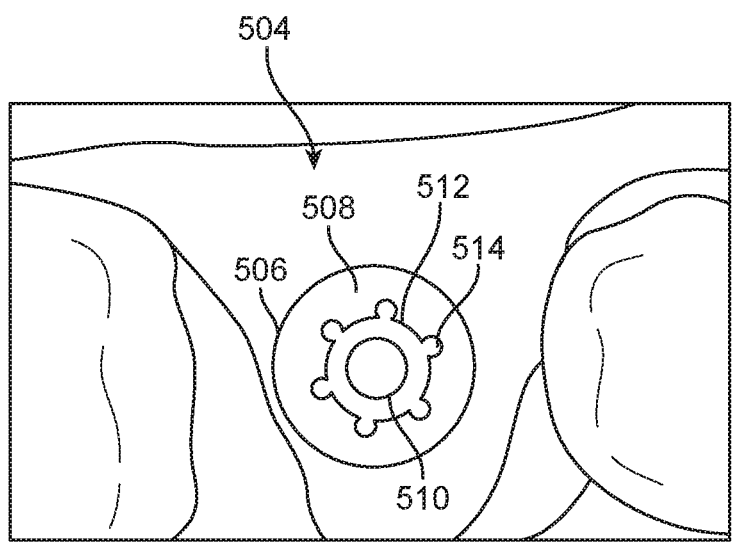
FIG. 5B is a top view of the of the unitary dental model of FIG. 5A, in accordance with many embodiments.

FIG. 5A illustrates a unitary dental model 500 fabricated using a CNC milling process, in accordance with many embodiments. The unitary dental model 500 includes surfaces 502 corresponding to teeth and gingiva of the patient and integrally formed structures 504 for retaining an abutment at a specified position and orientation in the model 500. FIG. 5B is a top view of the model 500. The integrally formed structures 504 include an opening 506 and a channel having a first portion 508 for receiving an abutment and a second portion 510 for receiving a fastener for the abutment. The first portion 508 can include a cavity 512 shaped to receive a corresponding structure of the abutment. Although the cavity 512 is depicted as a hexagonal shape, other shapes can also be used, such as a circle, triangle, rectangle, square, star, or other polygonal shape, as well as suitable combinations thereof. In embodiments where the cavity 512 is produced by a CNC milling procedure, it may be difficult to fabricate the corners of the cavity 512 with sufficient clearance to permit easy fit of the corresponding abutment structure into the cavity. Accordingly, the cavity 512 may be produced with a plurality of recesses 514 situated at or near the corners of the cavity 512. The configuration of each of the recesses 514 (e.g., size, shape, location) can be adapted to provide additional clearance so as to facilitate the insertion of the corresponding abutment structure into the cavity 512.

In step 440, an abutment is mounted to the unitary dental model. The abutment can be mounted using the integrally formed structures provided herein (e.g., the first portion 218 of the channel 210). The shape and orientation of the integrally formed structures may constrain the abutment to a specified position and orientation when coupled to the unitary dental model, such that the spatial disposition of the abutment is fixed relative to up to six degrees of freedom of movement.

In step 450, the abutment is secured to the unitary dental model. In many embodiments, the abutment is secured to the physical model by one or more fasteners (e.g., fastener 230 and/or nut 232). Alternatively, the abutment can be secured directly to the model by suitable fastening structures integrated into the model (e.g., integrated threading).

In step 460, a dental prosthesis is mounted onto the abutment, using techniques known to one of skill in the art.

Although the above steps show method 400 of creating a unitary dental model in accordance with many embodiments, a person of ordinary skill in the art will recognize many variations based on the teaching described herein. Some of the steps may comprise sub-steps. One or more steps of the method 400 may be performed with any suitable design and fabrication system, such as the embodiments described herein. Some of the steps may be optional, such as one or more of steps 410, 450, or 460. Optionally, some of the steps of the method 400 can be combined. For example, steps 420 and 430 can be combined, such that the unitary dental model is fabricated with the 3D topographical data provided in step 410.

Figure 6:
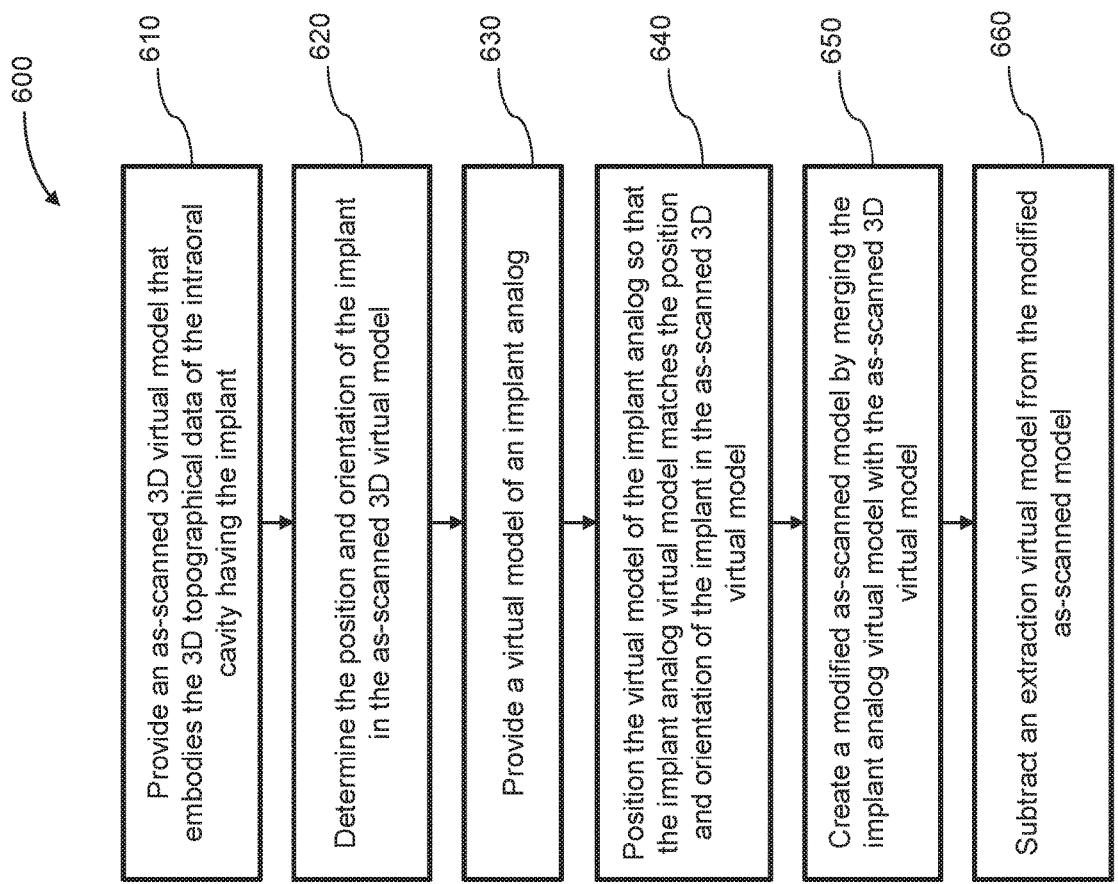
FIG. 6 illustrates a method for creating a virtual model of a patient's intraoral cavity, in accordance with many embodiments.

FIG. 6 illustrates a method 600 for creating a virtual model of a patient's intraoral cavity, in accordance with many embodiments. Any suitable system can be used to practice the method, such as the systems described herein. The steps of the method 600 can be combined or substituted with any suitable steps of the other methods disclosed herein.

In step 610, a first virtual model (hereinafter "as-scanned 3D virtual model") that embodies the 3D topographical data of the intraoral cavity having the implant is provided. The as-scanned 3D virtual model can be created from data obtained through any suitable method, such as data generated by scanning the patient's intraoral cavity or an impression of the patient's intraoral cavity. The scan data may include data corresponding to a scan body coupled to the implant in the intraoral cavity. In embodiments where an impression of the intraoral cavity is scanned, the scan data may include data corresponding to an impression of an impression body coupled to the implant. As previously described herein, the scan data may provide a representation of one or more structures of the scan body or impression body that enable the position and orientation of the implant to be determined. Optionally, the as-scanned virtual 3D model can be modified to remove model elements corresponding to components (e.g., the scan body or impression body coupled to the implant) that will not be present in the unitary dental model.

In step 620, the position and orientation of the implant in the as-scanned 3D virtual model is determined. In particular, the position and orientation of the implant structures that interface with the abutment (e.g., the coupling interface) can be determined. In many embodiments, the position and orientation is determined using one or more structures of a scan body or impression body that is coupled to the implant and scanned with the intraoral cavity, as described above. For example, the one or more structures can be identified (e.g., in an automated, semi-automated, or manual process) and used to position and orient a virtual model of the scan body or impression body relative to the as-scanned 3D virtual model, such as by registering the corresponding structures of the scan body or impression body virtual model to the identified structures in the as-scanned 3D virtual model. The scan body or impression body virtual model can then be used to determine the position and orientation of the implant, e.g., by registering an implant virtual model to the scan body or impression body virtual model. The registration of virtual models to each other may be automated, semi-automated, or performed manually based on user input. Alternatively or in combination, other structures of the intraoral cavity can be used to locate the implant, such as one or more structures of a healing abutment coupled to the implant.

In step 630, a virtual model of an implant analog is provided. The virtual model can be created from any suitable analog of the implant in the patient's intraoral cavity and by any suitable method, such as by 3D topographical scanning of the implant analog. In many embodiments, the implant analog and the implant include the same structures that are configured to receive and constrain the abutment at a specified position and orientation.

In step 640, a virtual model of the implant analog is positioned and oriented relative to the as-scanned 3D virtual model so that the implant analog virtual model matches the position and orientation of the implant in the as-scanned 3D virtual model. The implant analog virtual model may be located in the as-scanned 3D virtual model based on a previously determined position and orientation of an implant virtual model, as described above. In many embodiments, the implant analog virtual model is positioned and oriented such that the abutment interfacing structures of the implant analog virtual model match the position and orientation of the abutment interfacing structures of the implant in the as-scanned 3D virtual model. Any suitable method for positioning and orienting the implant analog virtual model relative to the as-scanned virtual model can be used. For example, the implant analog virtual model can be positioned and oriented relative to the as-scanned virtual model through an automated process using a computer system having suitable software, such as shape recognition software. Alternatively or in combination, the implant analog virtual model can be positioned and oriented relative to the as-scanned virtual model based on user input.

In step 650, a second virtual model (hereinafter "modified as-scanned model") is created by merging the implant analog virtual model with the as-scanned 3D virtual model. Any suitable method for merging virtual models can be used. For example, the merge can use suitable computer software to combine the virtual models into a single modified-as scanned model and remove duplicated model elements.

In step 660, an extraction virtual model can be subtracted from the modified as-scanned model. Any suitable method for subtracting an extraction virtual model from a virtual model can be used. In many, the subtraction of the extraction virtual model creates one or more integrally formed structures (e.g., opening 214, first portion 218 of channel 210) in the modified as-scanned model for receiving the abutment, as previously described herein. In many embodiments, the extraction virtual model can be also configured to create one or more structures (e.g., opening 216, second portion 220 of channel 210) to accommodate one or more fasteners configured to couple and/or fasten an abutment to a physical model of the modified as-scanned model, as previously described herein. Alternatively or in combination, the extraction virtual model can be configured to remove one or more virtual model elements corresponding to a body coupled to the implant (e.g., a scan body or impression body).

Although the above steps show method 600 of creating a virtual model in accordance with many embodiments, a person of ordinary skill in the art will recognize many variations based on the teaching described herein. Some of the steps may comprise sub-steps. Many of the steps may be repeated as often as appropriate for the modeling process. One or more steps of the method 600 may be performed with any design and fabrication system, such as the embodiments described herein. One or more steps may be performed based on user input (e.g., from a dental practitioner, technician, etc.). Alternatively or in combination, one or more steps may be performed in an automated or semi-automated manner. Some of the steps may be optional, such as one or more of steps 630, 640, and 650. In many embodiments, the integrally formed structures can be created in the virtual model without using an implant analog virtual model. For example, the integrally formed structures can be shaped, positioned, and oriented in the virtual model based on information regarding the shape of the abutment and the position and orientation of the implant in the virtual model. The abutment shape information can be provided using a virtual abutment model (e.g., created from 3D topographical scanning of the abutment) that can be combined with the as-scanned 3D virtual model to create one or more of the integrally formed structures. As another example, the integrally formed structures can be created using information regarding the shape of the implant, such as the shape of the coupling interface of the implant.

Figure 7:
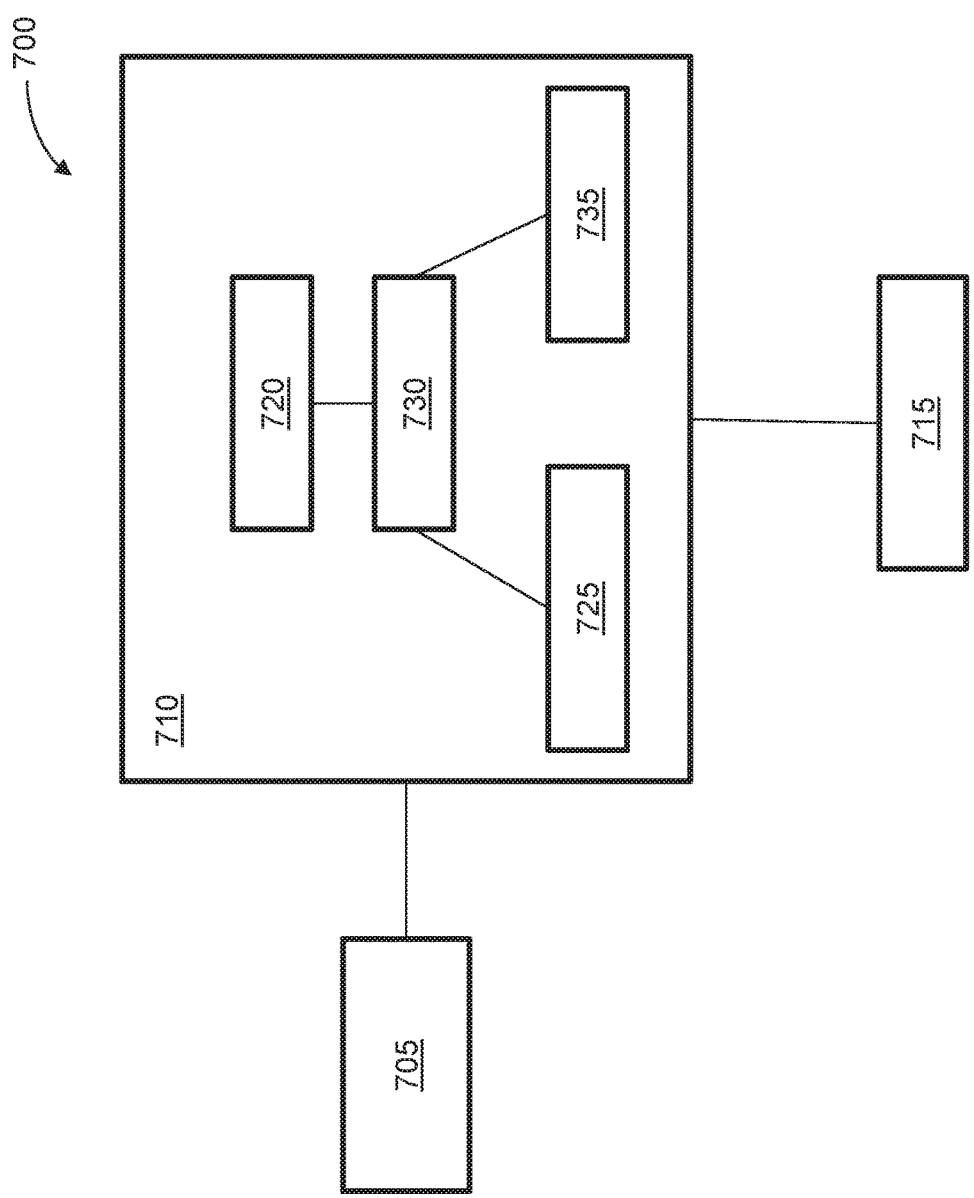
FIG. 7 illustrates a system for creating a unitary dental model, in accordance with many embodiments.

FIG. 7 illustrates a system 700 for creating a unitary dental model, in accordance with many embodiments. The system can be used to practice any suitable steps of the methods previously described herein. The system 700 can include a scanner 705, a computer system 710, and a manufacturing system 715 for fabricating a unitary dental model having the integrally formed structures discussed herein. The scanner 705 can be any suitable scanner for obtaining 3D topographical data of an intraoral cavity of the patient having a dental implant, such as an intraoral scanner or desktop scanner. The scanner 705 can be operatively coupled to and controlled by the computer system 710. Alternatively or in combination, the scanner 705 can be controlled by a different computer system, and the data obtained by scanner 705 can be transmitted to computer system 710 through a suitable data transmission method. For example, scanning can be performed by scanner 705 in a dental clinic, and the scanning data can be sent to computer system 710 at a facility remote to the dental clinic.

The computer system 710 can include an input interface 720 (e.g., a mouse, a keyboard, or a touch screen), an output device or display 725 (e.g., a screen, a monitor, or a printer), a processing unit 730, and a memory 735. The memory 735 can include memory storing instructions that can be executed by the processing unit 730. The computer system 710 can include suitable software (e.g., virtual modeling software) for creating a virtual model from the 3D topographical data obtained by scanner 705. For example, the memory storing instructions can include suitable computer code to be executed by the processing unit 730 to create a virtual model in accordance with the methods provided herein. The instructions can also include suitable computer code to be executed by the processing unit 730 to generate output for controlling a manufacturing system 715 to fabricate a unitary dental model having the integrally formed structures described herein.

The manufacturing system 715 can include a computer-controlled manufacturing system configured for manufacturing a physical dental model from a virtual model based on output from the computer system 710. Any suitable computer-controlled manufacturing system can be used, such as a manufacturing system suitable for performing stereolithography, 3D printing, CNC milling, and the like. The manufacturing system 715 can be controlled by one or more processors of any suitable computer system, such as the computer system 710. Alternatively or in combination, the manufacturing system 715 can be controlled by a different computer system than the computer system 710, and the data output by computer system 710 can be transmitted to the manufacturing system 715 by a suitable data transmission method. For example, the computer system 710 can be used to create a virtual model at a modeling facility, and the virtual modeling data can be transmitted to a remote manufacturing facility to control manufacturing system 715.

The various techniques described herein may be partially or fully implemented using code that is storable upon storage media and computer readable media, and executable by one or more processors of a computer system. The processor can comprise array logic such as programmable array logic (hereinafter PAL), configured to perform the techniques described herein. Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for creating a unitary dental model of an intraoral cavity of a patient having a dental implant; the method comprising:
   receiving three-dimensional (3D) topographical data of the intraoral cavity having the dental implant; and
   fabricating the unitary dental model with the 3D topographical data, the unitary dental model comprising,
      a physical surface representative of gingival tissue of the patient, and
      a channel extending through the unitary dental model and shaped and oriented to receive an abutment corresponding to a physical abutment to be connected to the dental implant, wherein the channel extends to an opening in the physical surface, the channel comprising a first portion and a second portion, the first portion shaped to receive and constrain a corresponding structure of the abutment to a position and orientation and having a shape complementary to the shape of the abutment, the second portion shaped to receive a fastener to couple the abutment to the unitary dental model,
   wherein the first portion comprises a shoulder shaped to receive the corresponding structure of the abutment in order to position the abutment along the channel, the shoulder extending from a surface of the first portion and to a surface of the second portion, and
   wherein the shape of the first portion constrains the corresponding structure of the abutment to the position and orientation while the shoulder is in contact with the corresponding structure of the abutment.

2. The method of claim 1, further comprising:
   mounting the abutment to the unitary dental model via the first portion of the channel; and
   securing the abutment to the unitary dental model using the fastener received within the second portion of the channel.

3. The method of claim 1, wherein using the 3D topographical data to fabricate the unitary dental model comprises:
   positioning a virtual model of an implant analog relative to an as-scanned three-dimensional (3D) virtual model that embodies the 3D topographical data of the intraoral cavity having the dental implant so that the implant analog virtual model matches the position and orientation of the dental implant in the as-scanned 3D virtual model; and
   modifying the as-scanned 3D virtual model by merging the implant analog virtual model with the as-scanned 3D virtual model, thereby creating a modified as-scanned model.

4. The method of claim 3, further comprising subtracting an extraction virtual model from the modified as-scanned model so as to one or more of: a) create the second portion of the channel shaped to receive the fastener, or b) remove one or more virtual model elements corresponding to a scan body or an impression body coupled with the dental implant in the as-scanned 3D virtual model.

5. The method of claim 3, further comprising modifying one or more portions of the modified as-scanned model in order to provide a desired amount of clearance between the first portion and the corresponding structure of the abutment.

6. The method of claim 1, wherein the fabricating step is performed using a computer-controlled material removing process.

7. The method of claim 1, wherein the physical surface comprises physical models of one or more teeth and a physical model of gingival tissue extending between the one or more teeth, and wherein the physical models of the one or more teeth are representative of one or more teeth of the intraoral cavity near the dental implant.

8. The method of claim 1, wherein the opening comprises a maximum cross-sectional dimension sized larger than a maximum cross-sectional dimension of the second portion.

9. The method of claim 1, wherein the first portion is shaped to correspond to a portion of the dental implant that receives and constrains a corresponding structure of the physical abutment.

10. The method of claim 1, wherein the second portion extends to an opening in a bottom surface opposite the physical surface, and wherein the opening in the bottom surface is shaped to accommodate a nut for securing the abutment and fastener to the unitary dental model.

11. The method of claim 1, wherein the first portion is shaped to receive and constrain the corresponding structure of the abutment to a predetermined position and orientation.

12. The method of claim 11, wherein the predetermined position and orientation corresponds to a position and orientation of the physical abutment when connected to the dental implant in the intraoral cavity.

13. The method of claim 11, wherein the channel is an elongate channel comprising a longitudinal axis, and the predetermined position and orientation is defined by one or more of the longitudinal axis, shoulder, or opening.

14. The method of claim 13, wherein the predetermined orientation comprises a predetermined rotational angle about the longitudinal axis.

15. The method of claim 13, wherein the predetermined orientation comprises a predetermined rotational angle away from the longitudinal axis.

16. The method of claim 13, wherein the corresponding structure of the abutment comprises a lower engagement surface and the shoulder is shaped to receive and mate with the lower engagement surface in order to position the corresponding structure at a location along the longitudinal axis.

17. A system for modeling of an intraoral cavity of a patient having a dental implant; the system comprising:
   one or more processors;

memory storing instructions that, when executed by the one or more processors, cause the one or more processors to:
receive three-dimensional (3D) topographical data of the intraoral cavity having the dental implant; and
generate a virtual model with the 3D topographical data, the virtual model comprising,
a virtual surface representative of gingival tissue of the patient, and
a channel extending through the virtual model and shaped and oriented to receive a virtual abutment model corresponding to one or more of a physical abutment to be connected to the dental implant or an abutment to be connected to a unitary dental model fabricated from the virtual model, wherein the channel extends to an opening in the virtual surface, the channel comprising a first portion and a second portion, the first portion shaped to receive and constrain a corresponding structure of the virtual abutment model to a position and orientation and having a shape complementary to the shape of the virtual abutment model, the second portion shaped to receive a virtual fastener model corresponding to a fastener used to couple the abutment to the unitary dental model,
wherein the first portion comprises a shoulder shaped to receive the corresponding structure of the virtual abutment model in order to position the virtual abutment model along the channel, the shoulder extending from a surface of the first portion and to a surface of the second portion, and
wherein the shape of the first portion constrains the corresponding structure of the virtual abutment model to the position and orientation while the shoulder is in contact with the corresponding structure of the virtual abutment model.

18. The system of claim 17, wherein the instructions, when executed by the one or more processors, cause the one or more processors to:
position a virtual model of an implant analog relative to an as-scanned three-dimensional (3D) virtual model that embodies the 3D topographical data of the intraoral cavity having the dental implant so that the implant analog virtual model matches the position and orientation of the dental implant in the as-scanned 3D virtual model; and
modify the as-scanned 3D virtual model by merging the implant analog virtual model with the as-scanned 3D virtual model, thereby creating a modified as-scanned model.

19. The system of claim 18, wherein the instructions, when executed by the one or more processors, cause the one or more processors to subtract an extraction virtual model from the modified as-scanned model so as to one or more of: a) create the second portion of the channel shaped to receive the virtual fastener model, or b) remove one or more virtual model elements corresponding to a scan body or an impression body coupled with the dental implant in the as-scanned virtual model.

20. The system of claim 17, wherein the instructions, when executed by the one or more processors, cause the one or more processors to generate output configured to control a fabrication machine to fabricate a unitary dental model corresponding to the virtual model.

21. A computer-implemented method for creating a virtual model of an intraoral cavity of a patient having a dental implant, the method comprising:
receiving three-dimensional (3D) topographical data of the intraoral cavity having the dental implant; and
generating a virtual model with the 3D topographical data, the virtual model comprising,
a virtual surface representative of gingival tissue of the patient, and
a channel extending through the virtual model and shaped and oriented to receive a virtual abutment model corresponding to one or more of a physical abutment to be connected to the dental implant or an abutment to be connected to a unitary dental model fabricated from the virtual model, wherein the channel extends to an opening in the virtual surface, the channel comprising a first portion and a second portion, the first portion shaped to receive and constrain a corresponding structure of the virtual abutment model to a position and orientation and having a shape complementary to the shape of the virtual abutment model, the second portion shaped to receive a virtual fastener model corresponding to a fastener used to couple the abutment to the unitary dental model,
wherein the first portion comprises a shoulder shaped to receive the corresponding structure of the virtual abutment model in order to position the virtual abutment model along the channel, the shoulder extending from a surface of the first portion and to a surface of the second portion, and
wherein the shape of the first portion constrains the corresponding structure of the virtual abutment model to the position and orientation while the shoulder is in contact with the corresponding structure of the virtual abutment model.

22. The computer-implemented method of claim 21, wherein said using the 3D topographical data to create the virtual model comprises:
positioning a virtual model of an implant analog relative to an as-scanned three-dimensional (3D) virtual model that embodies the 3D topographical data of the intraoral cavity having the dental implant so that the implant analog virtual model matches the position and orientation of the dental implant in the as-scanned 3D virtual model; and
modifying the as-scanned 3D virtual model by merging the implant analog virtual model with the as-scanned 3D virtual model, thereby creating a modified as-scanned model.

23. The computer-implemented method of claim 22, wherein said using the 3D topographical data to create the virtual model further comprises subtracting an extraction virtual model from the modified as-scanned model so as to at least one of: a) create the second portion of the channel shaped to receive the virtual fastener model, and b) remove one or more virtual model elements corresponding to a scan body or an impression body coupled with the dental implant in the as-scanned 3D virtual model.

* * * * *